(12) United States Patent
Xu et al.

(10) Patent No.: US 9,943,524 B2
(45) Date of Patent: Apr. 17, 2018

(54) USE OF ALKALOID IN PREPARING PHARMACEUTICAL COMPOSITIONS FOR PREVENTING OR TREATING PULMONARY FIBROSIS

(71) Applicant: China Pharmaceutical University, Nanjing, Jiangsu (CN)

(72) Inventors: Xianghong Xu, Jiangsu (CN); Mian Zhang, Jiangsu (CN); Juan Xiang, Jiangsu (CN); Yanhui He, Jiangsu (CN); Yan Wu, Jiangsu (CN)

(73) Assignee: China Pharmaceutical University, Nanjing, Jiangsu (CN)

( * ) Notice: Subject to any disclaimer, the term of this patent is extended or adjusted under 35 U.S.C. 154(b) by 0 days.

(21) Appl. No.: 15/328,758

(22) PCT Filed: Jun. 17, 2015

(86) PCT No.: PCT/CN2015/081658
§ 371 (c)(1),
(2) Date: Jan. 24, 2017

(87) PCT Pub. No.: WO2016/015524
PCT Pub. Date: Feb. 4, 2016

(65) Prior Publication Data
US 2017/0216306 A1    Aug. 3, 2017

(30) Foreign Application Priority Data

Jul. 30, 2014    (CN) .......................... 2014 1 0376837

(51) Int. Cl.
*A61K 31/55*    (2006.01)

(52) U.S. Cl.
CPC .................................. *A61K 31/55* (2013.01)

(58) Field of Classification Search
None
See application file for complete search history.

(56) References Cited

U.S. PATENT DOCUMENTS

2003/0229071 A1* 12/2003 Lin ...................... C07D 487/06
514/214.01

FOREIGN PATENT DOCUMENTS

| CN | 1453279 A | 11/2003 |
| CN | 102961656 A | 3/2013 |
| CN | 104188973 A | 12/2014 |

OTHER PUBLICATIONS

MedBroad Cast (2017).*

* cited by examiner

*Primary Examiner* — Shirley V Gembeh
(74) *Attorney, Agent, or Firm* — Young Basile Hanlon & MacFarlane, P.C.

(57) ABSTRACT

A new use of a compound as indicated in structural formula I in preparing medications for preventing and/or treating pulmonary fibrosis includes the compound having the structure as indicated in structural formula 1 that substantially reduces the inflammation of diseased lung tissue, lowers the concentration of fibrosis factors TGF-βI in diseased lung tissue, decreases the excessive deposition of collagen in diseased lung tissue, and has substantial prevention and treatment effectiveness against fibrosis.

6 Claims, 7 Drawing Sheets

USE OF ALKALOID IN PREPARING PHARMACEUTICAL COMPOSITIONS FOR PREVENTING OR TREATING PULMONARY FIBROSIS

CROSS-REFERENCE TO RELATED APPLICATION(S)

This application claims priority to Chinese application 201410376837.6 filed on Jul. 30, 2014, the content of which is hereby incorporated by reference in its entirety.

TECHNICAL FIELD

The present invention relates to an alkaloid possessing activity of anti-pulmonary fibrosis, specifically a use of alkaloid having the structure as indicated in structural Formula I in preparing pharmaceutical compositions for preventing or treating pulmonary fibrosis.

BACKGROUND

Pulmonary fibrosis (PF) is a kind of disease with normal lung tissue structure changing and function losing, which is caused by cell excessive repairing and excessive accumulation of extracellular matrix resulting from sustained alveolus injury due to pneumonia. Clinical manifestations of this disease include dyspnea, shortness of breath and tiredness. This disease is characterized by a continuous progress. Say popularly, pulmonary fibrosis is that the alveolus is gradually replaced by fiber materials, and the lung tissue becomes tough and thick, therefore the ability of oxygen exchange of the lung tissue fades away. The patients will suffer respiratory difficulty and respiratory failure in turn as a result of anoxia until death. In the past 20 years, the incidence of pulmonary fibrosis is rising year by year because of the environmental pollution. At present, glucocorticoid and immunosuppressant, such as prednison, cytoxan and colchicines, are main drugs for treating the pulmonary fibrosis. Clinical practices of recent years have proved that drugs, such as glucocorticoid, antibiotic and immunosuppressant, can relieve early inflammation of alveolus and clinical symptoms of patients, but cannot suppress the development of fibrosis effectually. Furthermore, long-term uses of high doses of hormone and antibiotic not only lead to serious complications but also aggravate the process of fibrosis. Because the etiology and pathogenesis are unclear, the treatment of pulmonary fibrosis is still a difficult problem in the medicine field. Although new drugs are continually developed, there're no effective therapeutic methods and professional therapeutic drugs yet. The prognosis is poor, the mean survival time is only 3 years and five-year survival rate is less than 50%, therefore pulmonary fibrosis is called cancer but not cancer actually.

Pathogenesis of pulmonary fibrosis is still unclear, but it has a common feature that collagen metabolism in the body is out-of-balance and the synthesis of collagen exceeds the degradation of collagen. Therefore, the occurrence of pulmonary fibrosis results from the activation of cytokines and the dysregulation of collagen metabolism. In recent years, studies focus on cytokines which play an important role in regulating proliferation, transformation and secretion of lung fibroblasts. Inflammation and fibrosis of tissue can be observed in most of the pulmonary fibrosis patients. Sustained Inflammation injuries may cause fibrosis. Cytokines, such as TGF-$\beta$1, FGFs, PDGFs and VEGFs, play a key role in the process of the occurrence of pulmonary fibrosis. Wherein TGF-$\beta$1, a recognized pro-fibrogenic marker, is a mediator which is most closely associated with the occurrence and formation of pulmonary fibrosis. The up-regulation of TGF-$\beta$1 can activate the classic Smad signaling pathway downstream, and stimulate cells to synthesize and excrete a large number of extracellular matrix. With the increase of deposition of extracellular matrix and epithelial-mesenchymal transition in the process of fibrosis, development of fibrosis is accelerated. Based on the above reasons, TGF-$\beta$1 has become the main target of anti-fibrosis. The contents of hydroxyproline in lung tissues indicate the contents of collagen and the expression level of TGF-$\beta$1 shows the possible mechanism of drugs intervening in pulmonary fibrosis. That is, drugs can relieve pulmonary fibrosis, though decreasing the level of TGF-$\beta$1 to inhibit the TGF-$\beta$1/Smad pathway rather than anti-inflammatory. For an example, pirfenidone, a drug which has just come into the market in Japan, India and European Union, can inhibit the pro-fibrogenic factors such as TGF-$\beta$1 but have clinical side effects such as photosensitization.

Cough is one of the common symptoms in respiratory diseases. Similar to other respiratory diseases, early pulmonary fibrosis also shows general symptoms like cough. Although there is some relationship between cough and pulmonary fibrosis, in fact they are totally different. Strictly speaking, cough is a pattern of manifestation in respiratory diseases but not a real illness. Cough may occur in early stage or developing period of pulmonary fibrosis, and symptoms including cough and asthma occurring in early fibrosis can be alleviated by using anti-cough drugs, but the drugs will be ineffective if the condition is serious and in this situation only hormone and antibiotic can be used to alleviate the symptoms of the disease. However, the above treatments only scratch the surface but cannot radically cure or prevent pulmonary fibrosis. Furthermore, a long-term uses of hormone and antibiotic may even aggravate pulmonary fibrosis.

In summary, there still lacks effective treatment for pulmonary fibrosis and it is urgent to develop new drugs with better curative effect to relieve even cure the pulmonary fibrosis.

Traditional Chinese Medicine stemonae belongs to Stemona of Stemonaceae, and has the function of moistening lung along with gas, suppressing cough, deinsectization and delousing. Stemonae is mainly used in treating for pertussis, tuberculosis, new or old cough, and treatment of enterobiasis of head and body in clinic. Stemona alkaloids are the major bioactive components of stemonae. Studies have shown that compounds such as tuberostemonine J, tuberostemonine H, isostenine and neotuberostemonine isolated from stemona tuberosa have a very good antitussive effect in cough of guinea pig induced by citric acid. Wherein, isostenine and neotuberostemonine have a similar antitussive effect as codein while tuberostemonine J and tuberostemonine H have a weaker antitussive effect than that of codein. Studies have also shown that antitussive activities of croomine, neotuberostemonine and stemoninine in stemona tuberosa are similar while that of tuberostemonine is weaker. Besides, mechanism researches have shown that neotuberostemonine, tuberostemonine and stemoninine target the peripheral cough reflex pathway which belongs to peripheral antitussive, while croomine works by inhibiting cough center. Although cough is one of the symptoms in pulmonary fibrosis, there is no any report showing that anti-cough drugs can improve or treat pulmonary fibrosis so far.

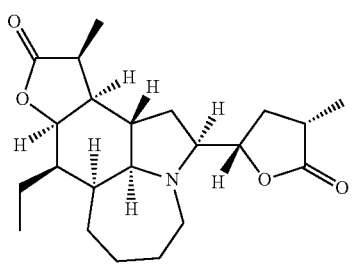

Tuberostemonine J

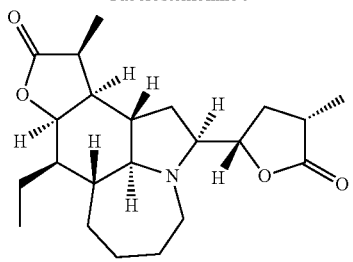

Tuberostemonine H

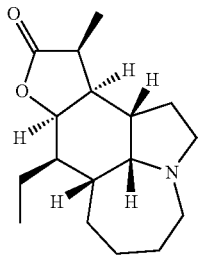

Isostenine

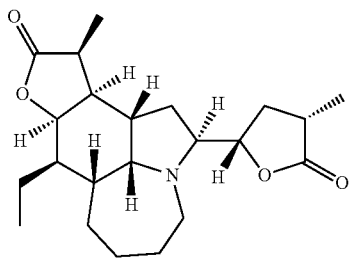

Neotuberostemonine

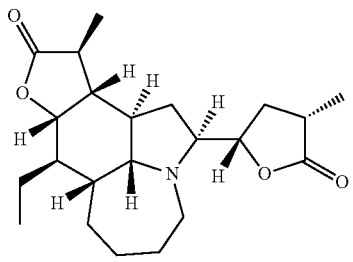

Tuberostemonine

There are few patents regarding stemona alkaloids and most of them are relating to preparation methods of total alkaloids or cough suppressing and deinsectization of alkaloids. Besides, there is only one patent (201210149954.X) regarding alkaloid represented by Formula (I) and the alkaloid is used in preparation of acetylcholinesterase inhibitors. There are no any reports regarding effects of stemona tuberosa alkaloids in preventing or treating pulmonary fibrosis and application of the drugs in treating pulmonary fibrosis.

SUMMARY

Aiming to the deficiencies that effective drugs for preventing or treating pulmonary fibrosis are inadequate, the present invention discloses a new use of alkaloid having the structure as indicated in structural Formula I, which can effectively prevent or treat pulmonary fibrosis.

The technical solution of present application is: a use of alkaloid having the structure as indicated in structural Formula I in preparing pharmaceutical compositions for preventing or treating pulmonary fibrosis.

The formula I is:

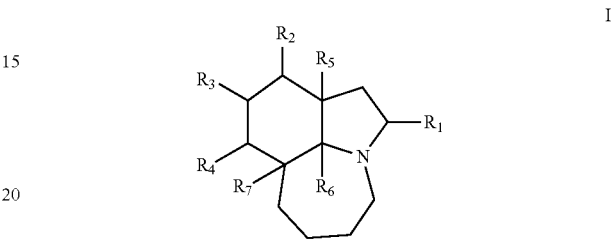

I

Wherein:

$R_1$ is selected from H, α or β OH, α or β COOH, α or β halogen substitution group, α or β alkoxy groups, α or β alkyl group; α or β alpha-methyl-gamma-butyrolactone;

$R_2$ is any selected from H, α or β OH, α or β COOH, α or β halogen substitution group, α or β alkoxy groups, α or β alkyl group;

$R_3$ is any selected from H, α or β OH, α or β COOH, α or β halogen substitution group, α or β alkoxy groups, α or β alkyl group;

Or, $R_2$ and $R_3$ are cyclized as the following structure by α or β configuration:

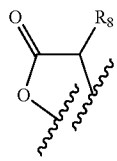

Wherein: $R_8$ is selected from α or β alkyl group;

$R_4$ is selected from α or β alkyl group;

$R_5$ is selected from α or β H;

$R_6$ is any selected from α or β H, α or β OH;

$R_7$ is selected from α or β H.

A use of compounds having the structure as indicated in structural Formula Ia in preparing pharmaceutical compositions for preventing and/or treating pulmonary fibrosis.

The formula Ia is:

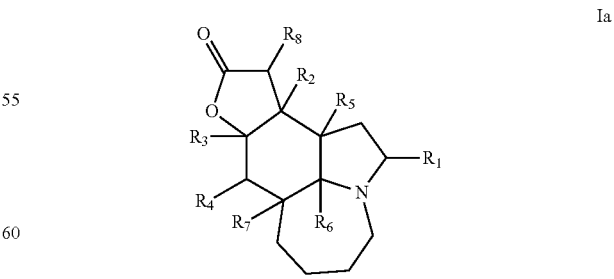

Ia

Wherein:

$R_1$ is selected from H, α or β OH, α or β COOH, α or β halogen substitution group, α or β alkoxy groups, α or β alkyl group; α or β alpha-methyl-gamma-butyrolactone;

$R_2$ is any selected from α or β H;
$R_3$ is any selected from α or β H;
$R_4$ is selected from α or β alkyl group;
$R_5$ is selected from α or β H;
$R_6$ is any selected from α or β H, α or β OH;
$R_7$ is selected from α or β H;
$R_8$ is selected from α or β alkyl group.

The use is characterized in that the compounds are alkaloids having the structure as indicated in structural Formula or pharmaceutical derivatives thereof.

The use is characterized in that pharmaceutical derivatives of the compounds are salts or esters of alkaloids having the structure as indicated in structural Formula I.

The use is characterized in that the pharmaceutical compositions include at least one active ingredient such as alkaloids having the structure as indicated in structural Formula I and pharmaceutical carrier.

The use is characterized in that the pharmaceutical compositions include 0.01%~99% (mass percent) alkaloids having the structure as indicated in structural Formula I and 0.01%~99% (mass percent) pharmaceutical carrier.

The "pulmonary fibrosis" in present application refers to pulmonary fibrosis of persons or animals caused by various reasons, and characterized in pathological changes of idiopathic pulmonary fibrosis.

The "preventing" refers to that pulmonary fibrosis can be prevented or alleviated by using drugs in such situation that factors which may cause pulmonary fibrosis have existed. The "treating" refers to alleviating the degree of pulmonary fibrosis, or curing pulmonary fibrosis, or slowing down the progress of pulmonary fibrosis.

Salts or esters of alkaloids refer to pharmaceutically-acceptable salts, esters and other forms.

The pharmaceutical compositions include at least one active ingredient, which has the effect in preventing or treating pulmonary fibrosis, such as alkaloids having the structure as indicated in structural Formula I and pharmaceutical carrier. Said active ingredient has the effect in preventing or treating pulmonary fibrosis. The active ingredients refer to alkaloids (Formula I) alone or with other compounds. The pharmaceutical carriers include pharmaceutically-acceptable excipients, fillers, diluents, and so on. In the pharmaceutical compositions, the content of alkaloids having the structure as indicated in structural Formula I is 0.01%~99%, the content of pharmaceutical carrier is 0.01%~99%, percentage refers to mass percentage.

There is no special restriction for the forms of the pharmaceutical compositions. The forms can be solid, semisolid or liquid, and can also be aqueous solution, non-aqueous solution or suspension. Route can be oral administration, intramuscular injection, intravenous administration, intradermal or subcutaneous injections. The daily dose of pharmaceutical compositions is 0.01~1000 mg, preferably 1~500 mg.

The alkaloids (Formula I) could be used alone or with other drugs to prevent or treat pulmonary fibrosis.

Alkaloids (Formula I) in present application are prepared and isolated from stemonaceae (purity>98%). Other raw materials and reagents are all commercially-available.

Advantages

1. As is shown by alkaloids having the structure as indicated in structural Formula I, the present invention provides a compound for preventing or treating pulmonary fibrosis. The in vitro experiment shows that the compounds can significantly prevent or treat mice pulmonary fibrosis induced by bleomycin, and obviously relieve pulmonary fibrosis. Therefore, the alkaloids can be used in preparing drugs for treating pulmonary fibrosis. Meanwhile, experiment has also shown that general anti-cough drugs are ineffective in preventing or treating pulmonary fibrosis. The present invention firstly discovers the effect of anti-pulmonary fibrosis of various compounds (compounds I-VIII) having the structure as indicated in structural Formula I, which have not revealed in the previous literature so far.

Specifically:

The present invention has shown that compounds possessing mother nucleus structure as indicated in structural Formula I, such as compounds I-VIII, have significantly effects in preventing and/or treating pulmonary fibrosis (embodiment 3). Surveys on activity of compounds I and VII (containing R1 side chain) together with VIII (no R1 side chain) have further shown that structures having the structure as indicated in structural Formula I have obvious effect of anti-pulmonary fibrosis. Multi-index animal experiments have shown that the compounds are more effective than the positive contrast medicine pirfenidone which has just come into the market in Japan. The compounds in present invention can obviously decrease the mortality of pulmonary fibrosis mice induced by bleomycin, the lung index of model mice, the extent of pulmonary fibrosis of model mice, and the contents of Hyp and pro-fibrogenic factor TGF-β1 in lung tissue. As mentioned above, compounds having the structure as indicated in structural Formula I can relieve lung inflammation of mice induced by bleomycin and reduce the accumulation of lung collagen. Results in present invention have provided a scientific basis for compounds having the structure as indicated in structural Formula I using in pharmaceutical compositions for preventing and/or treating pulmonary fibrosis.

2. Experiment materials referred in present invention, are taken from various stemonae, such as stemona tuberosa, stemona sessilifolia Miq., and stemona japonica Miq., are inexpensive and can easily obtained. Attempts to obtain the materials though synthetics have been reported.

BRIEF DESCRIPTION OF THE DRAWINGS

Wherein, FIG. 1A: Content of Hydroxyproline; FIG. 1B: HE stained pathological sections; FIG. 1C: Masson stained pathological sections. Wherein, 1:sham operation group, 2:model group, 3:pentoxyverine, 4:pirfenidone, 5:compound I, 6:compound II, 7:compound III, 8:compound IV, 9:compound V, 10:compound VI, 11:compound VII, 12:compound VIII. Compared with sham operation group, #P<0.05, ##P<0.01; compared with model group, *P<0.05, **P<0.01.

DETAILED DESCRIPTION

Figure 1A:
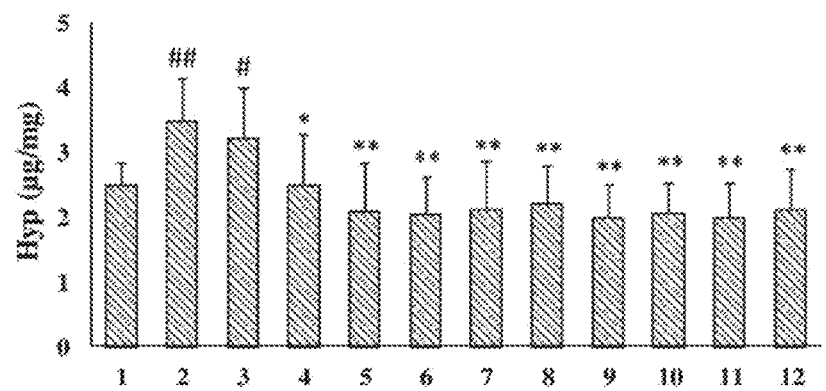
FIGS. 1A-1C show the effects of 8 alkaloids and pentoxyverine on pulmonary fibrosis mice induced by bleomycin.

Embodiment 1: Preparation and Structure Identification of Alkaloids

1. Medicinal Material and Reagents

The medicinal material is the dried roots of Stemona tuberosa Lour, and is purchased from Anguo medicine market, Hebei. Ethanol, dichloromethane, methanol and other reagents are all analytical grade.

Extraction and Isolation

Stemona tuberosa Lour is extracted with 90% ethanol by infiltrating, until the detection results of TLC show that the condensing percolation solution has no bismuth potassium iodide reactivity. Adjust the pH of condensing percolation solution to 1-2 by adding 5% diluted hydrochloric acid, then filter the condensing percolation solution to obtain filtrate, then adjust the pH of the filtrate to 10 by adding concentrated ammonia, then extract the aqueous layer with chloroform to get the total alkaloids, then separate the total alkaloids by silica gel column chromatography. Wherein, dichloromethane-methanol (100:0~1:5) is used in gradient elution. Based on results of TLC, the same effluent is blended and then separated by silica gel column chromatography repeatedly. Compound I and compound VII are obtained by partial isolation with eluent of dichloromethane-methanol (100:0), and the rest is isolated by preparative HPLC method with eluent of acetonitrile-water (42:58) to get compound II. Compound IV and compound III are obtained by partial isolation with eluent of dichloromethane-methanol (100:2), and the rest is isolated by preparative HPLC method with eluent of acetonitrile-water (23:77) to get compound V and compound VI. Compound VIII is obtained by partial isolation with eluent of dichloromethane-methanol (100:4). Purities of the above compounds are over 99% after HPLC analysis.

3. Structure Identification

Compound I (Tuberostemonine): colorless raphide (methanol), improved bismuth potassium iodide reactivity is positive.

ESI-MS (m/z: 376[M+H]+). $^1$HNMR (CDCl$_3$, 300 MHz) δ:1.80 (1H, m, H-1), 2.18 (1H, m, H-2 α), 1.10 (1H, m, H-2β), 3.43 (1H, m, H-3), 3.47 (1H, m, H-5α), 2.67 (1H, m, H-5β), 1.57 (1H, m, H-8), 1.82 (1H, m, H-9), 3.07 (1H, dd, J=3.5, 4.0 Hz, H-9α), 1.55 (1H, m, H-10), 4.44 (1H, dd, J=3.0, 3.5 Hz, H-11), 2.00 (1H, m, H-12), 2.41 (1H, dq, J=6.5, 7.5 Hz, H-13), 1.28 (3H, d, J=7.0 Hz, H-15), 1.52 (1H, m, H-16), 0.96 (3H, t, J=7.5 Hz, H-17), 4.31 (1H, m, H-18), 2.38 (1H, ddd, J=5.5, 13.5, 15.5 Hz, H-19), 2.60 (1H, ddq, J=7.0, 5.5, 12.0 Hz, H-20), 1.26 (3H, d, J=7.0 Hz, H-22). $^{13}$C NMR (CDCl$_3$, 75 MHz) δ: 41.6 (C-1), 32.1 (C-2), 65.0 (C-3), 48.1 (C-5), 28.1 (C-6), 29.9 (C-7), 30.4 (C-8), 40.7 (C-9), 63.6 (C-9a), 45.0 (C-10), 80.3 (C-11), 47.3 (C-12), 40.9 (C-13), 179.2 (C-14), 14.7 (C-15), 24.3 (C-16), 11.2 (C-17), 81.4 (C-18), 34.6 (C-19), 34.8 (C-20), 179.4 (C-21), 14.9 (C-22).

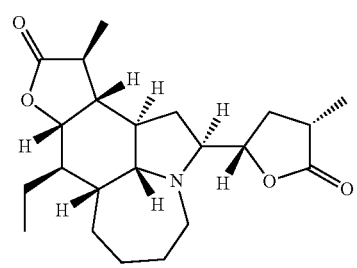

Compound I

Compound II (Tuberostemonine A): colorless raphide (methanol), improved bismuth potassium iodide reactivity is positive, ESI-MS (m/z:376[M+H]+). $^1$HNMR (CDCl$_3$, 300 MHz) δ:1.81 (1H, m, H-1), 1.84 (1H, m, H-2), 1.60 (1H, m, H-2), 3.09 (1H, m, H-3), 2.98 (1H, m, H-5), 2.44 (1H, m, H-5), 1.65 (1H, m, H-8), 1.57 (1H, m, H-9), 2.63 (1H, dd, J=3.5, 4.0 Hz, H-9α), 1.42 (1H, m, H-10), 4.44 (1H, dd, J=3.0, 3.5 Hz, H-11), 2.01 (1H, m, H-12), 2.33 (1H, dq, J=6.5, 7.5 Hz, H-13), 1.26 (3H, d, J=7.0 Hz, H-15), 1.64 (1H, m, H-16), 0.91 (3H, t, J=7.5 Hz, H-17), 4.31 (1H, m, H-18), 2.37 (1H, ddd, J=5.5, 13.5, 15.5 Hz, H-19), 2.69 (1H, ddq, J=7.0, 5.5, 12.0 Hz, H-20), 1.30 (3H, d, J=7.0 Hz, H-22). $^{13}$C NMR (CDCl$_3$, 75 MHz) δ:41.4 (C-1), 32.6 (C-2), 65.1 (C-3), 53.3 (C-5), 26.0 (C-6), 29.9 (C-7), 29.9 (C-8), 40.6 (C-9), 68.3 (C-9a), 42.5 (C-10), 80.2 (C-11), 46.9 (C-12), 40.1 (C-13), 179.2 (C-14), 15.2 (C-15), 22.4 (C-16), 9.8 (C-17), 80.8 (C-18), 32.5 (C-19), 35.6 (C-20), 179.4 (C-21), 15.2 (C-22).

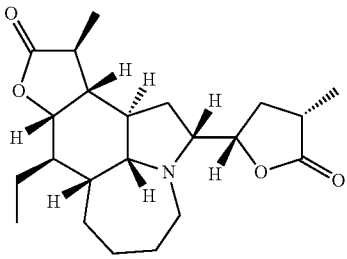

Compound II

Compound III (Tuberostemonine J): colorless raphide (methanol), improved bismuth potassium iodide reactivity is positive, ESI-MS (m/z:376[M+H]+). $^1$HNMR (CDCl$_3$, 300 MHz) δ:1.40~2.10 (15H, H-1, 2, 6~10, 12, 16, 19), 3.02 (2H, m, H-3, H-9a), 2.98 (1H, m, H-5), 2.74 (2H, H-5, H-13), 4.46 (1H, m, H-11), 1.18 (3H, d, J=7.5 Hz, H-15), 0.91 (3H, t, J=7.5 Hz, H-17), 4.39 (1H, m, H-18), 2.25 (1H, m, H-19), 2.50 (1H, m, H-20), 1.22 (3H, d, J=7.5 Hz, H-22). $^{13}$C NMR (CDCl$_3$, 75 MHz) δ:38.4 (C-1), 32.4 (C-2), 64.6 (C-3), 50.1 (C-5), 33.3 (C-6), 29.5 (C-7), 30.6 (C-8), 34.8 (C-9), 66.3 (C-9a), 34.5 (C-10), 80.3 (C-11), 41.1 (C-12), 45.8 (C-13), 179.3 (C-14), 11.6 (C-15), 25.4 (C-16), 12.9 (C-17), 81.2 (C-18), 34.3 (C-19), 45.1 (C-20), 179.2 (C-21), 14.8 (C-22).

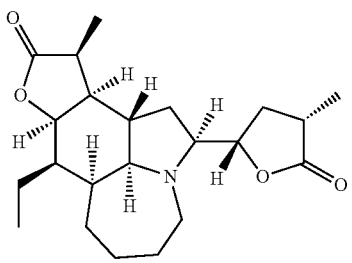

Compound III

Compound IV (Tuberostemonine H): colorless raphide (methanol), improved bismuth potassium iodide reactivity is positive, ESI-MS (m/z:376[M+H]+). $^1$HNMR (CDCl$_3$, 300 MHz) δ:1.30~2.00 (16H, H-1, 2, 6~10, 12, 16, 19), 3.20 (1H, m, H-3), 2.84 (1H, m, H-5), 2.78 (1H, m, H-5), 4.57 (1H, m, H-11), 2.61 (1H, m, H-13), 1.18 (3H, d, J=7.2 Hz, H-15), 1.00 (3H, t, J=7.2 Hz, H-17), 4.37 (1H, m, H-18), 2.35 (1H, m, H-19), 2.45 (1H, m, H-20), 1.22 (3H, d, J=7.2 Hz, H-22). $^{13}$C NMR (CDCl$_3$, 75 MHz) δ:41.9 (C-1), 31.1 (C-2), 78.0 (C-3), 54.7 (C-5), 27.3 (C-6), 24.1 (C-7), 27.1 (C-8), 41.1 (C-9), 67.5 (C-9a), 35.3 (C-10), 80.7 (C-11), 44.1 (C-12), 47.2 (C-13), 179.4 (C-14), 11.6 (C-15), 21.2 (C-16), 11.9 (C-17), 79.2 (C-18), 33.4 (C-19), 44.8 (C-20), 179.1 (C-21), 15.0 (C-22).

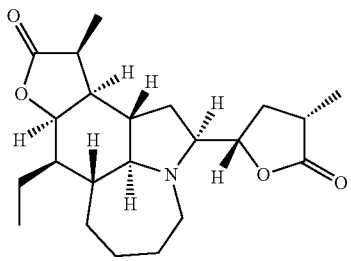

Compound IV

Compound V (Tuberostemonine N): colorless raphide (methanol) improved bismuth potassium iodide reactivity is positive, ESI-MS (m/z:376[M+H]+). $^1$HNMR (CDCl$_3$, 300 MHz) δ:1.75 (1H, m, H-1), 2.21 (1H, ddd, J=11.8, 6.3, 5.6 Hz, H-2α), 1.09 (1H, m, H-2β), 3.21 (1H, m, H-3), 3.31 (1H, dd, J=15.1, 6.3 Hz, H-5α), 2.79 (1H, m, H-5β), 1.33 (1H, m, H-6), 1.49 (1H, m, H-6), 1.19 (1H, m, H-7), 1.76 (1H, m, H-7), 1.60 (1H, m, H-8), 1.77 (1H, m, H-8), 2.01 (1H, d, J=12.0 Hz, H-9), 3.12 (1H, dd, J=11.9, 3.8 Hz, H-9a), 1.98 (1H, t, J=7.3 Hz, H-10), 4.20 (1H, dd, J=4.3, 1.8 Hz, H-11), 2.261 (1H, ddd, J=10.2, 7.3, 4.3 Hz, H-12), 2.81 (1H, dq, J=7.3, 7.3 Hz, H-13), 1.27 (3H, d, J=7.3 Hz, H-15), 1.42 (2H, m, H-16), 1.00 (3H, t, J=7.3 Hz, H-17), 4.19 (1H, m, H-18), 1.54 (1H, m, H-19α), 2.36 (1H, ddd, J=12.5, 8.4, 5.4 Hz, H-19β), 2.62 (1H, m, H-20), 1.27 (3H, d, J=7.1 Hz, H-22). $^{13}$C NMR (CDCl$_3$, 75 MHz) δ:35.2 (C-1), 33.7 (C-2), 65.2 (C-3), 50.7 (C-5), 26.9 (C-6), 29.8 (C-7), 32.8 (C-8), 40.1 (C-9), 64.2 (C-9a), 46.9 (C-10), 81.7 (C-11), 45.2 (C-12), 41.5 (C-13), 178.7 (C-14), 11.9 (C-15), 25.9 (C-16), 13.1 (C-17), 83.4 (C-18), 34.2 (C-19), 35.2 (C-20), 179.4 (C-21), 15.0 (C-22).

Compound V

Compound VI (Tuberostemonine K): colorless raphide (methanol), improved bismuth potassium iodide reactivity is positive, ESI-MS (m/z:376[M+H]+). $^1$HNMR (CDCl$_3$, 300 MHz) δ:1.79 (1H, m, H-1), 2.25 (1H, m, H-2α), 1.10 (1H, m, H-2β), 3.22 (1H, dd, J=9.0, 12.1 Hz, H-3), 2.81 (1H, dd, J=9.3, 15.1 Hz, H-5α), 3.41 (1H, dd, J=5.8, 9.3 Hz, H-5β), 1.28 (2H, m, H-6), 1.57 (2H, m, H-7), 1.06 (1H, m, H-8α), 1.88 (1H, m, H-8β), 1.89 (1H, m, H-9), 3.11 (1H, dd, J=3.9, 11.2 Hz, H-9a), 1.89 (1H, m, H-10), 4.20 (1H, d, J=2.0 Hz, H-11), 2.17 (1H, m, H-12), 2.88 (1H, dq, J=6.8, 7.4 Hz, H-13), 1.32 (3H, d, J=7.4 Hz, H-15), 1.2~1.4 (2H, m, H-16), 0.87 (3H, t, J=7.4 Hz, H-17), 4.26 (1H, m, H-18), 1.49 (1H, ddd, J=12 Hz, H-19α), 2.21 (1H, m, H-19β), 2.64 (1H, dq, J=4.0, 6.8 Hz, H-20), 1.23 (3H, d, J=6.8 Hz, H-22). $^{13}$C NMR (CDCl$_3$, 75 MHz) δ:35.6 (C-1), 33.6 (C-2), 65.5

(C-3), 50.4 (C-5), 27.6 (C-6), 30.1 (C-7), 33.0 (C-8), 47.3 (C-9), 64.1 (C-9a), 41.0 (C-10), 81.6 (C-11), 45.1 (C-12), 41.6 (C-13), 178.9 (C-14), 12.1 (C-15), 26.1 (C-16), 13.1 (C-17), 83.6 (C-18), 34.2 (C-19), 35.3 (C-20), 179.5 (C-21), 15.2 (C-22).

Compound VI

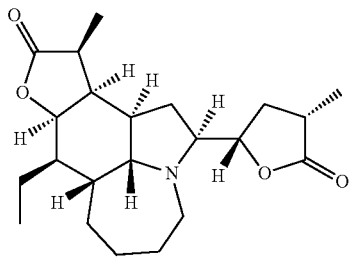

Compound VII (Neotuberostemonine): colorless raphide (methanol), mp: 160.5-162° C., improved bismuth potassium iodide reactivity is positive, ESI-MS (m/z:376[M+H]+). $^1$HNMR (CDCl$_3$, 500 MHz) δ:1.75 (1H, m, H-1), 1.65 (2H, m, H-2), 3.33 (1H, dd, J=7.5, 14.0 Hz, H-3), 3.08 (1H, m, H-5α), 2.98 (1H, m, H-5β), 1.94 (1H, m, H-8), 1.84 (1H, m, H-9), 3.21 (1H, dd, J=3.5, 4.0 Hz, H-9α), 1.72 (1H, m, H-10), 4.52 (1H, dd, J=3.0, 3.5 Hz, H-11), 2.10 (1H, m, H-12), 2.88 (1H, dq, J=6.5, 7.5 Hz, H-13), 1.23 (3H, d, J=7.0 Hz, H-15), 1.37 (1H, m, H-16), 1.00 (1H, t, J=7.5 Hz, H-17), 4.43 (1H, m, H-18), 2.39 (1H, ddd, J=5.5, 13.5, 15.5 Hz, H-19), 2.61 (1H, ddq, J=7.0, 5.5, 12.0 Hz, H-20), 1.26 (3H, d, J=7.0 Hz, H-22). $^{13}$C NMR (CDCl$_3$, 125 MHz) δ:37.3 (C-1), 32.6 (C-2), 67.7 (C-3), 51.0 (C-5), 29.1 (C-6), 22.8 (C-7), 28.6 (C-8), 35.9 (C-9), 67.2 (C-9a), 34.8 (C-10), 80.4 (C-11), 41.5 (C-12), 42.6 (C-13), 178.8 (C-14), 10.2 (C-15), 21.1 (C-16), 11.1 (C-17), 78.4 (C-18), 34.5 (C-19), 34.9 (C-20), 178.6 (C-21), 14.8 (C-22).

Compound VII

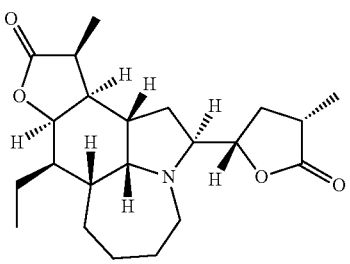

Compound VIII (Sessilifoline B): colorless column crystal (methanol), improved bismuth potassium iodide reactivity is positive, ESI-MS (m/z:278[M+H]+). $^1$H-NMR (CDCl$_3$, 500 MHz) δ:4.52 (1H, d, J=3.5 Hz, H-11), 3.29 (1H, m, H-3), 2.94 (1H, m, H-5), 2.86 (1H, m, H-13), 2.51 (2H, m, H-9α, H-3), 2.40 (1H, m, H-5), 2.30 (1H, m, H-12), 2.02 (1H, m, H-2), 1.93 (1H, m, H-9), 1.58 (1H, m, H-7), 1.21 (3H, d, J=7.5 Hz, 15-CH$_3$), 0.99 (3H, d, J=7.5 Hz, 17-CH$_3$). $^{13}$C-NMR (CDCl$_3$, 75 MHz) δ:37.3 (C-1), 29.9 (C-2), 55.9 (C-3), 55.8 (C-5), 28.1 (C-6), 21.0 (C-7), 28.0 (C-8), 34.0 (C-9), 71.1 (C-9a), 37.2 (C-10), 79.2 (C-11), 42.5 (C-12), 42.4 (C-13), 179.5 (C-14), 10.1 (C-15), 21.1 (C-16), 11.4 (C-17).

Compound VIII

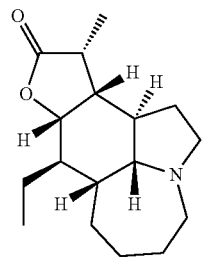

Embodiment 2: Preparation of Pulmonary Fibrosis Animal Model

1. Main Reagents and Experimental Animals

Bleomycin for experiment is purchased from Nippon Kayaku Co., Ltd., and the batch number is 730342.

C57BL/6 mice of SPF level for experiment (female, eight-week-old) are purchased from Comparative Medicine Center, Yangzhou University.

2. Model Preparation

Pulmonary fibrosis mice induced by bleomycin are the internationally recognized animal models for screening anti pulmonary fibrosis drugs. Acute lung injury of models induced by bleomycin is characterized by inflammation at the early stage. Then fibrosis begins to appear after 10 days around and lots of collagen is accumulated in lung. The pathological changes have close similarities with that of idiopathic pulmonary fibrosis. Although pathogenesis and mechanism of idiopathic pulmonary fibrosis are still unclear, pulmonary fibrosis and idiopathic pulmonary fibrosis induced by bleomycin are same that pulmonary injury causes immunity and inflammation, and leads to pathological changes of pulmonary fibrosis. Therefore, idiopathic pulmonary fibrosis and other pulmonary fibrosis disease causing by a series of various etiological factors which lead to similar pathological changes can be represented by pulmonary fibrosis induced by bleomycin.

Preparation Method of Pulmonary Fibrosis Animal Model

Female C57BL/6 mice (eight-week-old) are established for models after 7 days, the time is set for the mice to adapt to the environment. After fasts for overnight, the mice are anaesthetized by 3% chloral hydrate and fixed. Sterilize and incise neck skin longitudinally as little injury as possible. Split fascia and muscle with tweezers longitudinally and expose the windpipe. Then, about 35 μl (3.5 mg/kg) bleomycin are injected into windpipe with microinjector. Put the mice upright rapidly and rotate the mice for 3~5 minutes, so that bleomycin is able to enter into the pulmones uniformly. Observe the breathing of mice. Sterilize neck injury with 75% alcohol tampon and stitch the wound, then 1 drop or 2 drops of benzylpenicillin injection is/are dripped into the suture. Put the mice back into dry and clean cages, and feed them normally after waking up. Operations are done on operating table at about 60° C. Physiological saline using in injection is injected into windpipe of sham operation group.

Embodiment 3: Identification of Activity of 8 Alkaloids and Pentoxyverine Towards Anti Pulmonary Fibrosis in Mice This embodiment aims at studying the activity of anti-pulmonary fibrosis in mice by alkaloids obtained from embodiment 1, so as to identity whether the alkaloids have effects on anti-pulmonary fibrosis or not. The alkaloids mentioned above are all active ingredients of traditional Chinese medicine stemonae in cough suppressing. In order to study whether cough medicines have effect on anti-pulmonary fibrosis or not, this embodiment has chosen pentoxyverine citrate tablets, which are anti-cough drugs used frequently in clinic and are positive contrast medicine used frequently in pharmacology experiments of cough suppressing, to screen the activity of pulmonary fibrosis synchronously.

Main Reagents and Experimental Animals

Compounds I~VIII are obtained from embodiment 1, and their purities are all high than 98%. Pentoxyverine is purchased from Sinopharm Group Rong Sheng Pharmaceutical Co., Ltd., and the batch number is 13110221. Bleomycin for experiment is purchased from Nippon Kayaku Co., Ltd., and the batch number is 730342. Prifenidone (Positive drug) is purchased from Dalian Meilun Biological Technology Co., Ltd., and the purity is higher than 99%. Prifenidone, a new drug used in treating pulmonary fibrosis, is developed by American Marnac Inc. Development rights in Japan, Taiwan and Korea are given to Shionogi & Co., Ltd. The drug firstly come into the market in Japan in Oct. 17, 2008.

C57BL/6 mice of SPF level for experiment (female, eight-weeks-old) are purchased from Comparative Medicine Center, Yangzhou University.

2. Experimental Method

Experimental mice are randomly divided into 12 groups: 10 mice in model group, 10 mice in pentoxyverine group, and 5 mice in any other group. Group 1 is sham operation group, group 2 is model group, group 3 is pentoxyverine group, group 4 is positive drug pirfenidone group, groups 5-12 are compounds I-VIII administration group respectively. Models of groups 2-12 are established by using bleomycin with the same method used in embodiment 2. From the first day after successfully establishing model, 30 mg/kg pentoxyverine and 300 mg/kg pirfenidone are given to group 3 and group 4 by means of intragastric administration respectively. 30 mg/kg compounds I-VIII are given to groups 5-12 also by means of intragastric administration respectively. Besides, same doses of solvent are given to sham operation group and model group until the 21th day. After the last intragastric administration, the mice are killed to collect the lung tissue, and the right lobule is used for determining the content of hydroxyproline, while the left lobule is used for preparing pathological sections.

3. Experimental Results

Figure 1B:
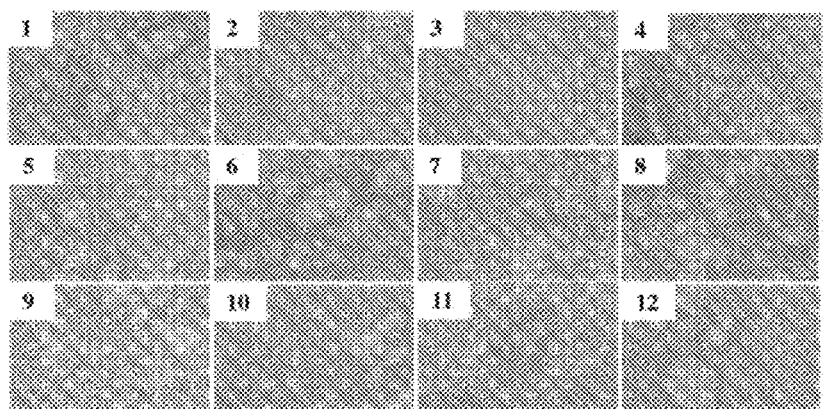

As is shown in FIG. 1A, comparing with sham operation group, the content of hydroxyproline in lung tissue of mice in model group increases significantly, indicating that the collagen has increased obviously and the fibrosis changes are serious. The 8 stemona alkaloids can significantly decrease the increasing degrees of the content of hydroxyproline caused by establishing mouse model and the alkaloids are more effective than the positive drug pirfenidone. The content of Hyp shows no significant difference in pentoxyverine group and model group, however, the content of Hyp in pentoxyverine group is significantly higher than that in sham operation group. As is shown in FIG. 1A and FIG. 1B, 21 days later after successfully establishing model, structures of pulmonary lobules of sham operation group are normal and the alveolar wall are complete without inflammation and fibrosis pathological changes. Obvious inflammation injury and masses of tissue begin to appear in lung of mice in model group, then the normal lung tissue disappears, alveolar is blocked and the collagen accumulates obviously. The 8 stemona alkaloids can significantly alleviate the pulmonary inflammation of mice caused by bleomycin and decrease the degree of pulmonary injury. Compounds I, II, III, VII and VIII enable the mice pulmonary to recover to nearly normal structure. Pentoxyverine cannot decrease the degree of pulmonary injury and fibrosis, the tissue section of pentoxyverine group is similar with that in model group, inflammatory injury is serious, alveolar is blocked, and the collagen accumulates obviously. The results illustrate that alkaloids possessing mother nucleus structure as indicated in structural Formula I have the significant effect in inhibiting or decreasing pulmonary fibrosis of model mice induced by bleomycin, however, anti-cough drugs are not able to improve pulmonary fibrosis of model mice.

Embodiment 4: The Effect of Compounds I, VII and VIII in Preventing or Treating Pulmonary Fibrosis Experimental Materials and Method (1) Main Reagents and Experimental Animals Compounds I, VII and VIII are obtained from embodiment 1, and purities are higher than 98%. Prifenidone (positive drug) is purchased from Dalian Meilun Biological Technology Co., Ltd., and the purity is higher than 99%.

Experimental animals are model mice which are prepared according to embodiment 2. The day when the model is established is counted as day 0.

(2) Experimental Method

Model animals are divided into prevention groups and treatment groups, then drugs are given to the two groups respectively. According to internationally methods of drug administration, drugs are given continuously to the prevention groups by means of intragastric administration from the second day after successfully establishing model to the 14th day, and drugs are given continuously to treatment groups by means of intragastric administration from the 8th day after successfully establishing model to the 21th day. Groups and dosage regimen are shown in tab.1.

TABLE 1

Groups and dosage regimen of pulmonary fibrosis mice after successfully establishing model

|  | NO. | Group | Amount of animals | Dosage and dosage regimen |
|---|---|---|---|---|
| Prevention groups (A) | 1 | Sham | 10 | Sham operation group, same doses of solvent, from the first day after establishing model to the 14th day |
|  | 2 | Model | 10 | Model group, same doses of solvent, from the first day after establishing model to the 14th day |
|  | 3 | I-30 | 10 | Compound I, 30 mg/kg, from the first day after establishing model to the 14th day |

TABLE 1-continued

Groups and dosage regimen of pulmonary fibrosis
mice after successfully establishing model

| | NO. | Group | Amount of animals | Dosage and dosage regimen |
|---|---|---|---|---|
| | 4 | I-60 | 10 | Compound I, 60 mg/kg, from the first day after establishing model to the 14th day |
| | 5 | VII-30 | 10 | Compound VII, 30 mg/kg, from the first day after establishing model to the 14th day |
| | 6 | VII-60 | 10 | Compound VII, 60 mg/kg, from the first day after establishing model to the 14th day |
| | 7 | VIII-30 | 10 | Compound VIII, 30 mg/kg, from the first day after establishing model to the 14th day |
| | 8 | VIII-60 | 10 | Compound VIII, 60 mg/kg, from the first day after establishing model to the 14th day |
| | 9 | Pir | 10 | Pirfenidone, 300 mg/kg, from the first day after establishing model to the 14th day |
| Treatment groups (B) | 1 | Sham | 10 | Sham operation group, same doses of solvent, from the 8th day after establishing model to the 21th day |
| | 2 | Model | 10 | Model group, same doses of solvent, from the 8th day after establishing model to the 21th day |
| | 3 | I-30 | 10 | Compound I, 30 mg/kg, from the 8th day after establishing model to the 21th day |
| | 4 | I-60 | 10 | Compound I, 60 mg/kg, from the 8th day after establishing model to the 21th day |
| | 5 | VII-30 | 10 | Compound VII, 30 mg/kg, from the 8th day after establishing model to the 21th day |
| | 6 | VII-60 | 10 | Compound VII, 60 mg/kg, from the 8th day after establishing model to the 21th day |
| | 7 | VIII-30 | 10 | Compound VIII, 30 mg/kg, from the 8th day after establishing model to the 21th day |
| | 8 | VIII-60 | 10 | Compound VIII, 60 mg/kg, from the 8th day after establishing model to the 21th day |
| | 9 | Pir | 10 | Pirfenidone, 300 mg/kg, from the 8th day after establishing model to the 21th day |

2. Determination of Mice Mortality

From the 0th day (the day when the model is established) to 14th day, drugs are given continuously to prevention groups. From the 8th day after successfully establishing model to 21th day, drugs are given continuously to treatment groups. Statistical analysis of death of animals in each group is carried on every day and the survival rate of animals in each group is calculated. Results are shown in tab.2.

As is shown in tab. 2, comparing with sham operation group, the mortality of model mice induced by bleomycin within 14 days is 20%, and the mortality within 21 days is 33%. Comparing with model group, the 3 compounds have protective effect on model mice, wherein compounds I and VII of prevention groups are more effective than compound VIII, and groups with lower dose (30 mg/kg) have better effect. In treatment groups, the 3 compounds have a similar effect in decreasing the mortality of mice, wherein groups with lower dose are slightly more effective than groups with higher dose. The present experimental results show that groups with lower dose have better protective effect on model mice, whether in prevention groups or treatment groups, than groups with higher dose. In general, the 3 compounds have better effect in decreasing the mortality of mice than positive drug pirfenidone.

TABLE 2

Death of prevention group and treatment group

| | Group | Sham | Model | I-30 | I-60 | VII-30 | VII-60 | VIII-30 | VIII-60 | Pir |
|---|---|---|---|---|---|---|---|---|---|---|
| Prevention groups | Amount of animal | 10 | 10 | 10 | 10 | 10 | 10 | 10 | 10 | 10 |
| | Mortality | 0 | 2 | 0 | 1 | 0 | 2 | 1 | 2 | 3 |
| | Survival rate (%) | 100 | 80 | 100 | 90 | 100 | 80 | 90 | 80 | 70 |
| Treatment groups | Amount of animal | 10 | 18 | 18 | 18 | 18 | 18 | 18 | 18 | 18 |
| | Mortality | 0 | 6 | 2 | 3 | 2 | 4 | 3 | 4 | 6 |
| | Survival rate (%) | 100 | 67 | 89 | 83 | 89 | 78 | 83 | 78 | 67 |

3. Detection of the Mice Lung Index

Figure 1C:
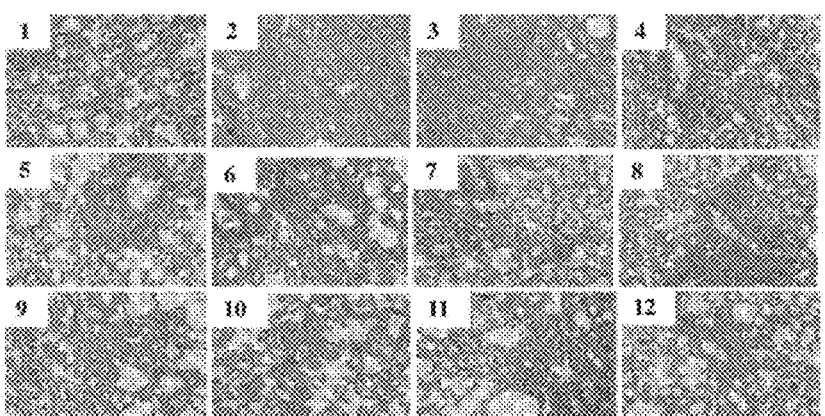
Figure 2:
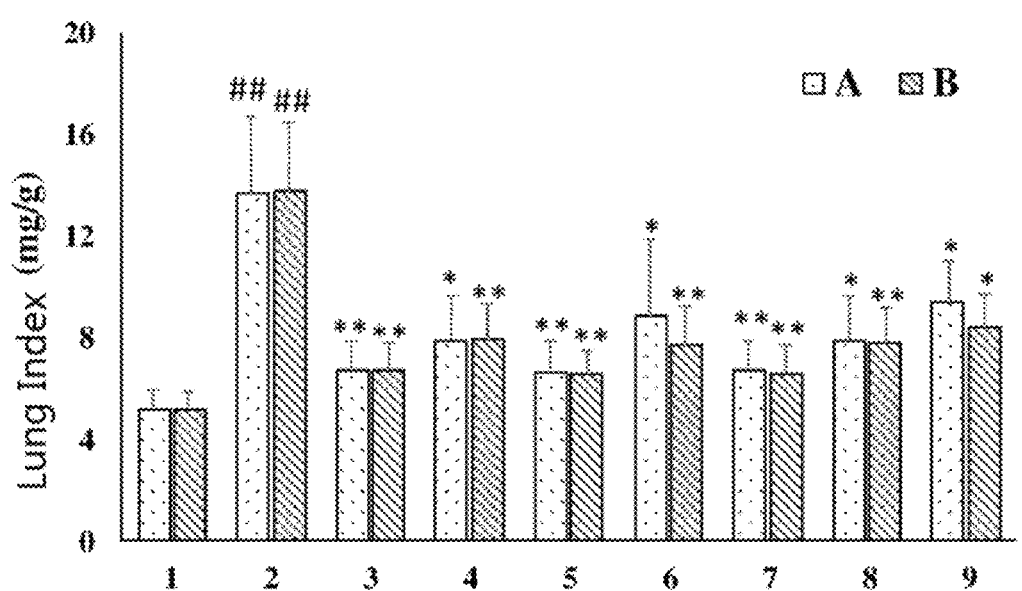
FIG. 2 shows the effects of 3 alkaloids on lung index of pulmonary fibrosis mice induced by bleomycin. Wherein, A: prevention groups, B: treatment group; 1:sham operation group, 2:model group, 3:compound I low-dose (30 mg/kg) group, 4:compound I high-dose (60 mg/kg) group, 5:compound VII low-dose (30 mg/kg) group, 6:compound VII high-dose (60 mg/kg) group, 7:compound VIII low-dose (30 mg/kg) group, 8:compound VIII high-dose (60 mg/kg) group, 9:pirfenidone (300 mg/kg) group. Compared with sham operation group, #P<0.05, ##P<0.01; compared with model group, *P<0.05, **P<0.01.

After the last intragastric administration, the mice are killed to strip and weigh the lung, and the lung index is the lung weight divided by mouse weight (FIG. 2). As is shown in FIGS. 1A-1C, the lung index of model group is significantly higher than that of sham operation group. The groups with doses of 30 and 60 mg/kg of compounds I, VII and VIII can significantly decrease the lung index of mice, whether in prevention groups or treatment groups, wherein group with lower dose in prevention groups has a better effect. In general, the 3 compounds have better effect in decreasing the mortality of mice than the positive drug pirfenidone.

4. HE Stained Pathological Evaluation and Inflammation Scores

Figure 3:
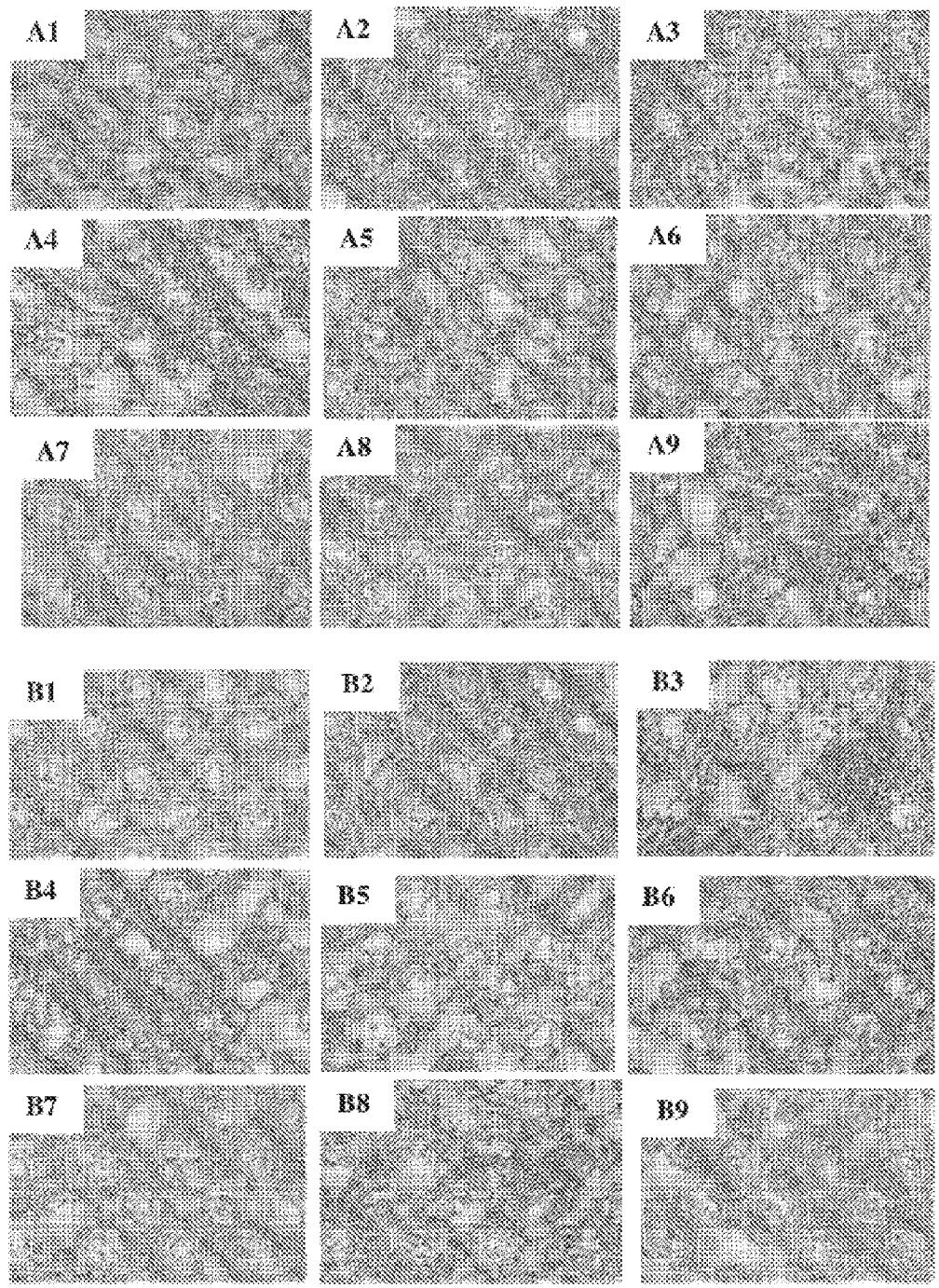
FIG. 3 shows the effects of 3 alkaloids on pulmonary histopathological changes of pulmonary fibrosis mice induced by bleomycin (HE stained). Wherein, A: prevention groups, B: treatment group; 1:sham operation group, 2:model group, 3:compound I low-dose (30 mg/kg) group, 4:compound I high-dose (60 mg/kg) group, 5:compound VII low-dose (30 mg/kg) group, 6:compound VII high-dose (60 mg/kg) group, 7:compound VIII low-dose (30 mg/kg) group, 8:compound VIII high-dose (60 mg/kg) group, 9:pirfenidone (300 mg/kg) group.

After the last intragastric administration, the mice are anaesthetized and killed to collect the lung tissue. Immerse the left lobule in 10% formalin, and embed it by paraffin after being fixed, then cut it into slices to observe the pathological changes by HE staining. As is shown in FIG. 3, structures of lobules of sham operation group are normal and the alveolar walls are complete without inflammation and fibrosis pathological changes. Obvious inflammation injury and masses of tissue begin to appear in lung of mice in model group, then the normal lung tissue disappears and alveolar is blocked. Whether in prevention groups or treatment groups, compounds I, VII and VIII can significantly alleviate the pulmonary inflammation caused by bleomycin and decrease the pulmonary injury, and recover lung to normal structure. The groups with lower dose (30 mg/kg) of the 3 compounds show better effect than the groups with higher dose. The pulmonary inflammation disappears and alveolar structure is clear in groups with lower dose.

Figure 4:
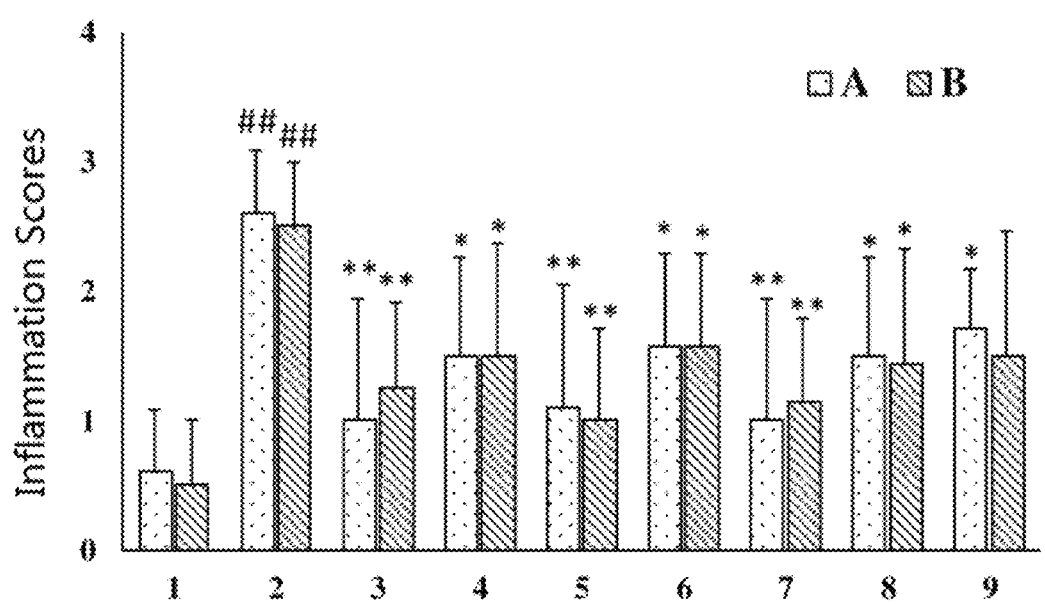
FIG. 4 shows the effects of 3 alkaloids on lung tissue inflammation scores of pulmonary fibrosis mice induced by bleomycin (HE stained). Wherein, A: prevention groups, B: treatment group; 1:sham operation group, 2:model group, 3:compound I low-dose (30 mg/kg) group, 4:compound I high-dose (60 mg/kg) group, 5:compound VII low-dose (30 mg/kg) group, 6:compound VII high-dose (60 mg/kg) group, 7:compound VIII low-dose (30 mg/kg) group, 8:compound VIII high-dose (60 mg/kg) group, 9:pirfenidone (300 mg/kg) group. Compared with sham operation group, #P<0.05, ##P<0.01; compared with model group, *P<0.05, **P<0.01.

Inflammatory classification semi quantitative statistics analysis is made according to results of HE staining. Grade 0 represents normal tissue or minimal inflammation change. Grade 1 (+) represents mild to moderate inflammation change, and lung tissue without obvious damage. Grade 2 (++) represents moderate to severe inflammation injury, and alveolar septum is thickened to form masses of tissue, or lung tissue with damage caused by partial area inflammation. Grade 3 (+++) represents severe inflammation injury, and structure of restricted regions in lung tissue is severely damaged, thus resulting in obliteration. Inflammation scores of prevention groups and treatment groups are shown in FIG. 4. Comparing with sham operation group, there is significantly pulmonary inflammation appearing in model mice induced by bleomycin. The groups with doses of 30, 60 mg/kg of compounds I, VII and VIII can significantly decrease the pulmonary inflammation induced by bleomycin. The groups with lower dose show better effect than the groups with higher dose. In general, the 3 compounds have better effect in decreasing the pulmonary inflammation than the positive drug pirfenidone.

5. Masson Stained Pathological Evaluation and Imaging Analysis

Figure 5:
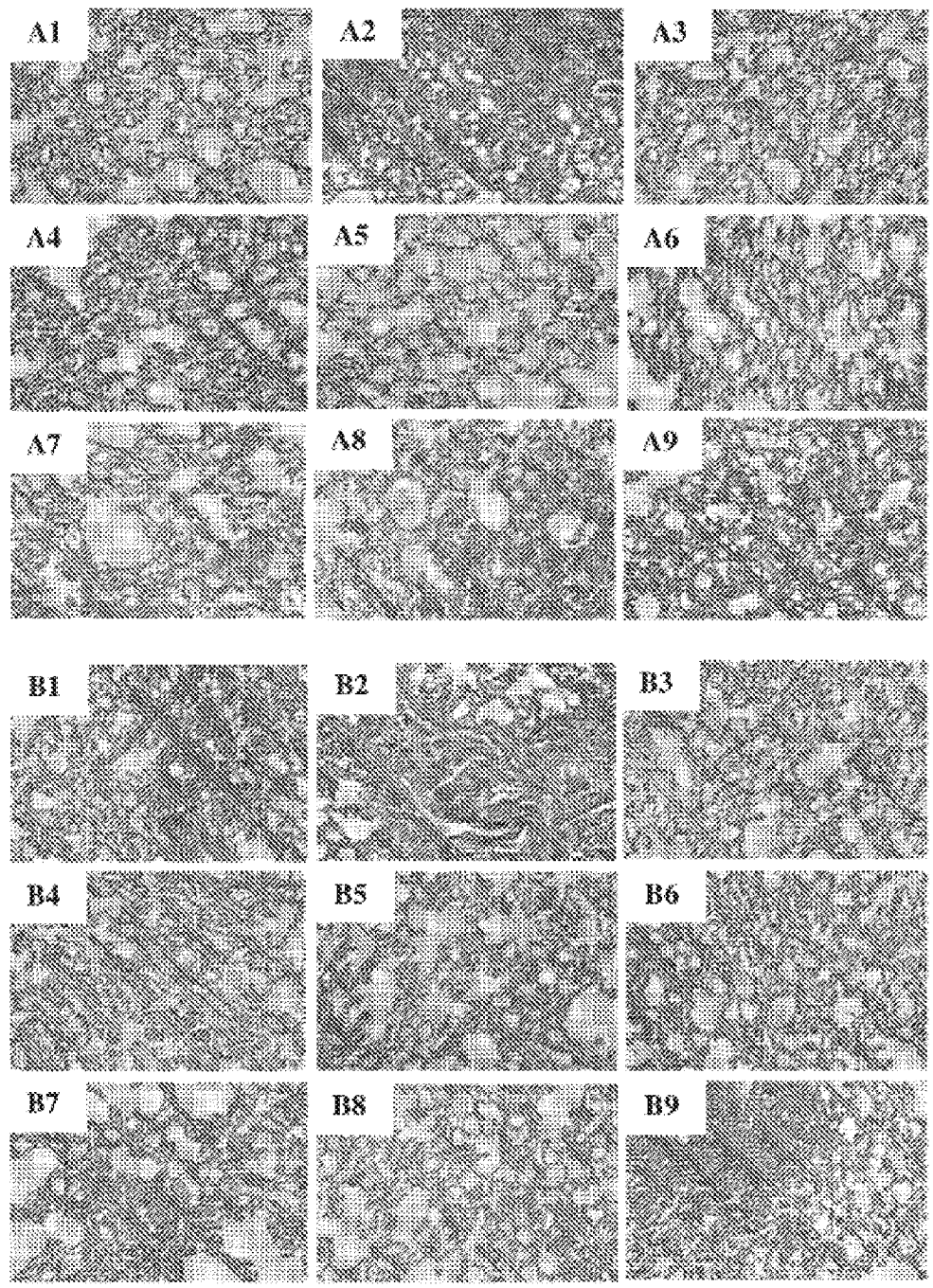
FIG. 5 shows the effects of 3 alkaloids on pulmonary histopathological changes of pulmonary fibrosis mice induced by bleomycin (Masson stained). Wherein, A: prevention groups, B: treatment group; 1:sham operation group, 2:model group, 3; compound I low-dose (30 mg/kg) group, 4:compound I high-dose (60 mg/kg) group, 5:compound VII low-dose (30 mg/kg) group, 6:compound VII high-dose (60 mg/kg) group, 7:compound VIII low-dose (30 mg/kg) group, 8:compound VIII high-dose (60 mg/kg) group, 9:pirfenidone (300 mg/kg) group.

Masson staining is a method aiming at specific staining of fibrillar collagen. After the last intragastric administration, the mice are anaesthetized and killed to collect the lung tissue. Immerse the left lobule in 10% formalin, and embed it by paraffin after being fixed, then is cut it into slices to observe the collagen deposition by Masson staining. The results of Masson staining in prevention groups and treatment groups are shown in FIG. 5. Semi quantitative analysis is made by using Image-Pro Plus6.0. Integrated optical density (IOD) of collagen in each visual field is measured after Masson staining. 5 samples are studied in each group and 5 visual fields are picked out from each group. Statistics analysis is made by calculating mean value which is considered as relative amount of collagen in each group. The analysis results of prevention groups and treatment groups are shown in FIG. 6.

Figure 6:
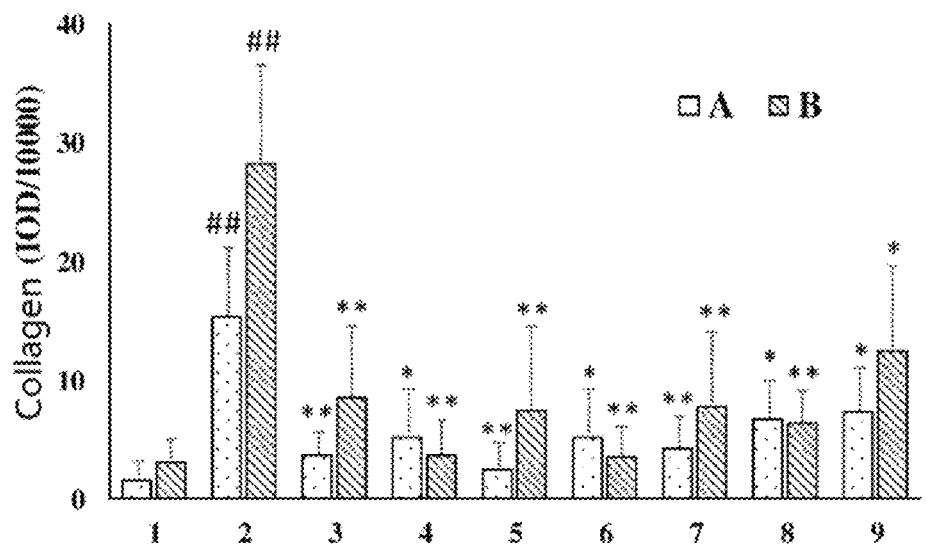
FIG. 6 shows the effects of 3 alkaloids on collagen contents of lung tissues of pulmonary fibrosis mice induced by bleomycin (Average optical density value statistics). Wherein, A: prevention groups, B: treatment group; 1:sham operation group, 2:model group, 3:compound I low-dose (30 mg/kg) group, 4:compound I high-dose (60 mg/kg) group, 5:compound VII low-dose (30 mg/kg) group, 6:compound VII high-dose (60 mg/kg) group, 7:compound VIII low-dose (30 mg/kg) group, 8:compound VIII high-dose (60 mg/kg) group, 9:pirfenidone (300 mg/kg) group. Compared with sham operation group, #P<0.05, ##P<0.01; compared with model group, *P<0.05, **P<0.01.

As is shown in FIGS. 5 and 6, there is no obvious Masson collagen deposition can be seen in mice pulmonary of sham operation group. Obvious Masson collagen deposition can be seen in mice pulmonary after giving bleomycin for 14 or 21 days, massive fibrosis tissues are formed, and fibrosis in 21th day is more severe than that in 14th day. The groups with doses of 30, 60 mg/kg of compounds I, VII and VIII can significantly decrease collagen deposition caused by bleomycin and the effect in decreasing pulmonary fibrosis is extremely obvious. Wherein, the groups with lower dose of the 3 compounds in prevention groups show better effect than the groups with higher dose, and the groups with higher dose of the 3 compounds in treatment groups show better effect than the groups with lower dose. In general, effects of compounds I and VII in decreasing the collagen deposition are slightly better than that of compound VIII, and the effects of 3 compounds are obviously more effective than that of the positive drug pirfenidone.

6. Content Determination of Hydroxyproline

Hydroxyproline mainly exists in collagen protein, but there is only a very small amounts in elastin proteins and it cannot found in other proteins. Therefore the content of collagen protein can be indicated by measuring the content of hydroxyproline, so as to evaluate the degree of pulmonary fibrosis. Method of test kit (which is purchased from Nanjing Jiancheng Biological Technology Co., Ltd.) according to specification is used in determination of hydroxyproline. Results can be seen in FIG. 7.

Figure 7:
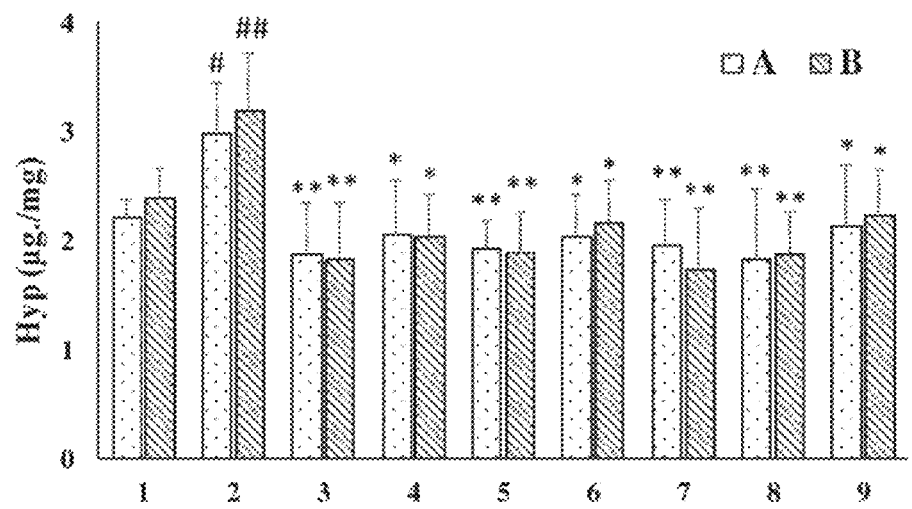
FIG. 7 shows the effects of 3 alkaloids on content of Hydroxyproline (Hyp) in lung tissue of pulmonary fibrosis mice induced by bleomycin. Wherein, A: prevention groups, B: treatment group; 1:sham operation group, 2:model group, 3:compound I low-dose (30 mg/kg) group, 4:compound I high-dose (60 mg/kg) group, 5:compound VII low-dose (30 mg/kg) group, 6:compound VII high-dose (60 mg/kg) group, 7:compound VIII low-dose (30 mg/kg) group, 8:compound VIII high-dose (60 mg/kg) group, 9:pirfenidone (300 mg/kg) group. Compared with sham operation group, #P<0.05, ##P<0.01; compared with model group, *P<0.05, **P<0.01.

As is shown in FIG. 7, comparing with sham operation group, the content of hydroxyproline in lung tissue of model mice significantly increases, indicating that there are serious fibrosis changes in lung tissue of model mice. Both the groups with lower dose (30 mg/kg) and the groups with higher dose (60 mg/kg) of compounds I, VII and VIII can effectively decrease the content of hydroxyproline in lung tissue of model mice whether in prevention groups or treatment groups. The effect of groups with lower dose is slightly better than the groups with higher dose, indicating that the 3 compounds can significantly improve the pulmonary fibrosis of model mice induced by bleomycin and decrease the collagen deposition.

7. ELISA Content Determination of TGF-β1

TGF-β1 is a universally recognized strong pro-fibrotic cytokine. It can stimulate the cells to synthesize and secrete extracellular matrix as well as exchange the activity of matrix-degrading enzyme component and directly increase the deposition of ECM. The progress of pulmonary fibrosis can be slowed down by decreasing the content of TGF-β1 in lung tissue. Elisa test kit (which is purchased from Shanghai Excell Biological Technology Co., Ltd.) according to specification is used in the determination of TGF-β1 in mice lung tissue. Results can be seen in FIG. 8.

Figure 8:
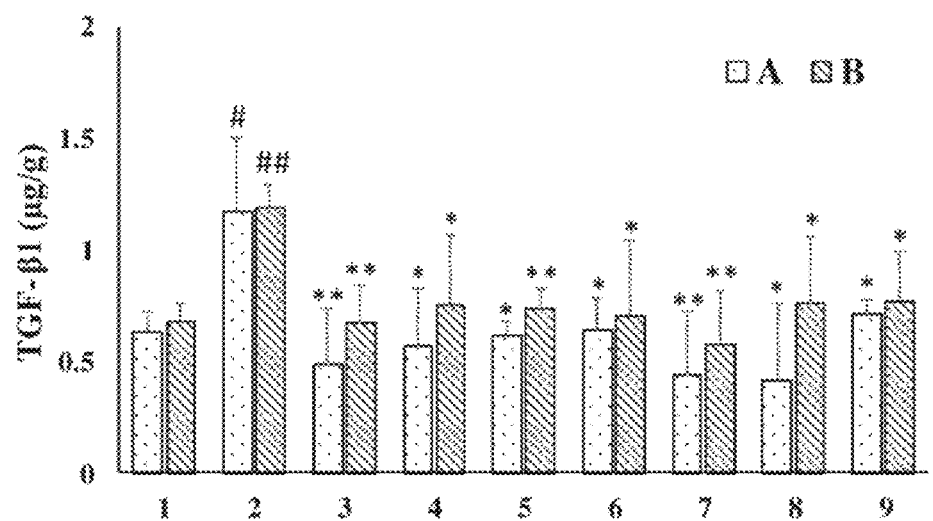
FIG. 8 shows the effects of 3 alkaloids on content of TGF-β1 in lung tissue of pulmonary fibrosis mice induced by bleomycin (ELISA). Wherein, A: prevention groups, B: treatment group; 1:sham operation group, 2:model group, 3:compound I low-dose (30 mg/kg) group, 4:compound I high-dose (60 mg/kg) group, 5:compound VII low-dose (30 mg/kg) group, 6:compound VII high-dose (60 mg/kg) group, 7:compound VIII low-dose (30 mg/kg) group, 8:compound VIII high-dose (60 mg/kg) group, 9:pirfenidone (300 mg/kg) group. Compared with sham operation group, #P<0.05, ##P<0.01; compared with model group, *P<0.05, **P<0.01.

As is shown in FIG. 8, comparing with sham operation group, the content of TGF-β1 in mice lung tissue after giving bleomycin significantly increases. Comparing with model group, both groups with lower dose (30 mg/kg) and groups with higher dose (60 mg/kg) of compounds I, VII and VIII can effectively decrease the content of TGF-β1 in model mice whether in prevention groups or treatment groups, and significantly reduce the degree of pulmonary fibrosis. Wherein, groups with lower dose are more effective than groups with higher dose and effects of compound I and VIII are slightly better than that of compound VII.

Discussion

The present invention has shown that compounds possessing mother nucleus structure as indicated in structural Formula I, such as compounds I-VIII, have significantly effect for preventing and/or treating pulmonary fibrosis (embodiment 3). Surveys on activity of compounds I and VII (containing R1 side chain) together with VIII (no R1 side chain) have further shown that structures as indicated in structural Formula I have the obvious effect of anti-pulmonary fibrosis. Multi-index animal experiments have shown that the compounds are more effective than the positive contrast medicine pirfenidone which has just come into the market in Japan. The compounds in present invention can obviously decrease the mortality of pulmonary fibrosis mice induced by bleomycin, the lung index of model mice and the extent of pulmonary fibrosis of model mice, and the contents of Hyp and pro-fibrogenic factor TGF-β1 in lung tissue. As mentioned above, compounds having the structure as indicated in structural Formula I can relieve lung inflammation of mice induced by bleomycin and reduce the accumulation of lung collagen.

Results in present invention have provided a scientific basis for compounds having the structure as indicated in structural Formula I using in pharmaceutical compositions for preventing and/or treating pulmonary fibrosis.

What is claimed is:

1. A method for treating pulmonary fibrosis, comprising administering a 30 mg/kg of compound of formula I

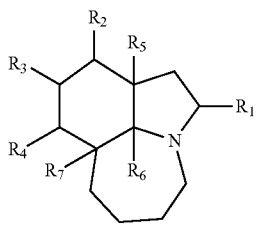

I wherein, $R_1$ is selected from H, a or R OH, a or R COOH, a or R halogen substitution group, a or R alkoxy groups, a or R alkyl group, and a or R alpha-methyl-gamma-butyrolactone; $R_2$ is selected from H, a or R OH, a or R COOH, a or R halogen substitution group, a or R alkoxy groups, and a or R alkyl group; $R_3$ is selected from H, a or R OH, a or R COOH, a or R halogen substitution group, a or p alkoxy groups, and a or p alkyl group; or $R_2$ and $R_3$ are cyclized as the following structure by a or 1 configuration:

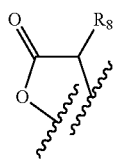

wherein, $R_8$ is selected from a or 1 alkyl group; $R_4$ is selected from a or 1 alkyl group; $R_5$ is selected from a or 1 H; $R_6$ is selected from a or 1 H, and a or 1 OH; and $R_7$ is selected from a or 1 H.

2. The method according to claim 1, wherein the compound is selected from compounds represented by structural Formula Ia:

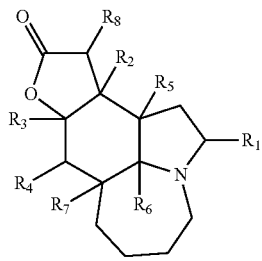

Ia wherein $R_1$ is selected from H, α or β OH, α or β COOH, α or β halogen substitution group, α or β alkoxy groups, α or β alkyl group, and α or β alpha-methyl-gamma-butyrolactone; $R_2$ is selected from α or β H; $R_3$ is selected from α or β H; $R_4$ is selected from α or β alkyl group; $R_5$ is selected from α or β H; $R_6$ is selected from α or β H and α or β OH; $R_7$ is selected from α or β H; and $R_8$ is selected from α or β alkyl group.

3. The method according to claim 2, wherein the compounds are alkaloids having the structure as indicated in structural Formula I or pharmaceutical derivatives thereof.

4. The method according to claim 3, wherein the pharmaceutical derivatives of the compounds are salts or esters of alkaloids having the structure as indicated in structural Formula I.

5. The method according to claim 1, wherein the pharmaceutical compositions include at least one active ingredient such as alkaloids having the structure as indicated in structural Formula I and a pharmaceutical carrier.

6. The use method according to claim 5, wherein the pharmaceutical compositions include ingredients with the following mass percentages: 0.01%-99% alkaloids having the structure as indicated in structural Formula I and 0.01%-99% of the pharmaceutical carrier.

* * * * *